(12) United States Patent
Nagaoka et al.

(10) Patent No.: US 9,882,136 B2
(45) Date of Patent: Jan. 30, 2018

(54) ORGANIC ELECTROLUMINESCENT DEVICE

(71) Applicant: Hodogaya Chemical Co., Ltd., Tokyo (JP)

(72) Inventors: Makoto Nagaoka, Tsukuba (JP);
Shuichi Hayashi, Tokyo (JP);
Motonori Tsuji, Tsukuba (JP);
Yoshikazu Aoki, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 493 days.

(21) Appl. No.: 14/402,219

(22) PCT Filed: Mar. 14, 2013

(86) PCT No.: PCT/JP2013/001705
§ 371 (c)(1),
(2) Date: Nov. 19, 2014

(87) PCT Pub. No.: WO2013/179536
PCT Pub. Date: Dec. 5, 2013

(65) Prior Publication Data
US 2015/0287920 A1    Oct. 8, 2015

Related U.S. Application Data

(60) Provisional application No. 61/653,584, filed on May 31, 2012.

(51) Int. Cl.
| | | |
|---|---|---|
| B32B 9/00 | (2006.01) |
| B32B 19/00 | (2006.01) |
| H01L 51/00 | (2006.01) |
| C07C 233/65 | (2006.01) |
| C07C 233/66 | (2006.01) |
| C07C 233/74 | (2006.01) |
| H01L 51/52 | (2006.01) |
| H01L 51/50 | (2006.01) |

(52) U.S. Cl.
CPC .......... *H01L 51/005* (2013.01); *C07C 233/65* (2013.01); *C07C 233/66* (2013.01); *C07C 233/74* (2013.01); *H01L 51/0052* (2013.01); *H01L 51/5275* (2013.01); *C07C 2601/08* (2017.05); *C07C 2601/14* (2017.05); *C07C 2601/18* (2017.05); *C07C 2603/74* (2017.05); *H01L 51/0059* (2013.01); *H01L 51/0072* (2013.01); *H01L 51/5012* (2013.01); *H01L 51/5056* (2013.01); *H01L 51/5072* (2013.01);

*H01L 51/5206* (2013.01); *H01L 51/5221* (2013.01); *H01L 51/5253* (2013.01)

(58) Field of Classification Search
None
See application file for complete search history.

(56) References Cited

U.S. PATENT DOCUMENTS

| | | |
|---|---|---|
| 6,235,823 B1 | 5/2001 | Ikeda et al. |
| 2011/0295010 A1 | 12/2011 | Shukla et al. |
| 2014/0225100 A1 | 8/2014 | Yokoyama et al. |

FOREIGN PATENT DOCUMENTS

| | | |
|---|---|---|
| JP | 05-262936 A | 10/1993 |
| JP | 06-200202 A | 7/1994 |
| WO | WO-2011/149699 A1 | 12/2011 |
| WO | WO-2013/038627 A1 | 3/2013 |

OTHER PUBLICATIONS

International Search Report dated May 21, 2013, issued for PCT/JP2013/001705.

*Primary Examiner* — Jeffrey H Murray
(74) *Attorney, Agent, or Firm* — Locke Lord LLP; James E. Armstrong, IV; Nicholas J. DiCeglie, Jr.

(57) ABSTRACT

An organic electroluminescent device having a capping layer composed of material having a high refractive index that involves only small differences in refractive indices measured in the blue, green, and red wavelength regions, excelling in thin film stability and durability and having no absorption in the respective wavelength ranges of blue, green, and red is provided to improve device characteristics of the organic electroluminescent device, particularly to greatly improve the coupling-out efficiency.

The organic electroluminescent device includes at least an anode, a hole transport layer, a light emitting layer, an electron transport layer, a cathode, and a capping layer in this order, wherein the capping layer contains a phthalic acid derivative represented by the following general formula

[Chemical Formula 1]

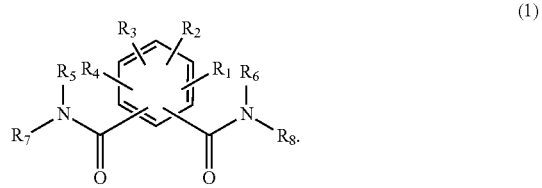

(1)

4 Claims, 1 Drawing Sheet

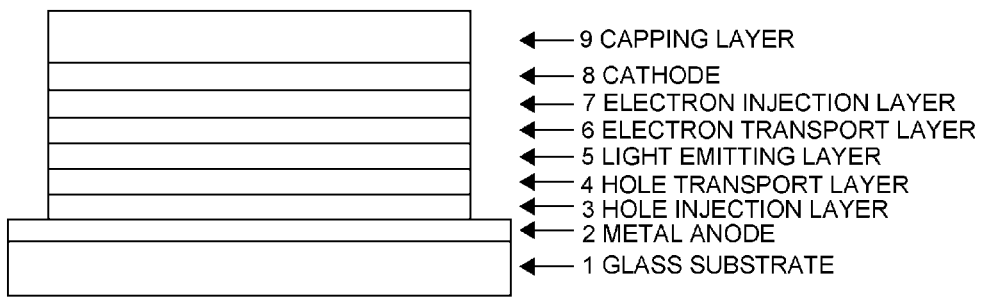

ORGANIC ELECTROLUMINESCENT DEVICE

TECHNICAL FIELD

The present invention relates to an organic electroluminescent device (hereinafter, referred to simply as "organic EL device"), a preferred self light-emitting device for various display devices. Specifically, the invention relates to organic EL devices that use specific phthalic acid derivatives, particularly to organic EL devices having greatly improved coupling-out efficiency.

BACKGROUND ART

The organic EL device is a self-emitting device, and has been actively studied for their brighter, superior viewability and ability to display clearer images compared with the liquid crystal device.

In 1987, C. W. Tang et al. at Eastman Kodak developed a laminated structure device using materials assigned with different roles, realizing practical applications of an organic EL device with organic materials. These researchers laminated an electron-transporting phosphor and a hole-transporting organic material, and injected the both charges into the phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic EL device. As an example, the various roles of the laminated structure are further subdivided to provide an electroluminescent device in which an anode, a hole injection layer, a hole transport layer, a light emitting layer, an electron transport layer, an electron injection layer, and a cathode are successively formed on a substrate, and a light-emitting device of a bottom-emission structure (the light is emitted from the bottom) having such a configuration has been proposed to realize high efficiency and durability (refer to Non-Patent Document 1, for example).

Light-emitting devices of a top-emission structure (the light is emitted from the top) that use high work-function metals for the anode have been used lately. An advantage of the light-emitting device of a top-emission structure is the wide emitter area, which is restricted by the pixel circuit in the light-emitting device of a bottom-emission structure. In the light-emitting device of a top-emission structure, the cathode uses a semi-transparent electrode such as LiF/Al/Ag (refer to Non-Patent Document 2, for example), Ca/Mg (refer to Non-Patent Document 3, for example), and LiF/MgAg.

In such light-emitting devices, total reflection occurs at the interface between a light emitting layer and other films when the emitted light from the light emitting layer is incident on other films above certain angles. The device can thus make use of only a part of the emitted light. For improved coupling-out efficiency, there have been proposed light-emitting devices that include a high-refractive-index "capping layer" on the outer side of a semi-transparent electrode of a lower refractive index (refer to Non-Patent Documents 2 and 3, for example).

The capping layer in a light-emitting device of a top-emission structure has been shown to effectively increase current efficiency about 1.7 fold in a light-emitting device using Ir(ppy)$_3$ as the light-emitting material, from 38 cd/A without a capping layer to 64 cd/A with a 60 nm-thick ZnSe capping layer. It has also been indicated that maximizing the transmittances of the semi-transparent electrode and the capping layer does not necessarily yield the maximum efficiency, and that the maximum coupling-out efficiency is determined by the interference effect (refer to Non-Patent Document 3, for example).

It has been proposed to use a fine metal mask for the formation of a capping layer. A problem of such metal masks, however, is that the registration accuracy decreases because of strains due to heat. Specifically, ZnSe has a high melting point of 1100° C. or more (refer to Non-Patent Document 3, for example), and cannot be vapor deposited on an accurate position with a fine mask. In fact, many inorganic materials have high vapor deposition temperatures, and are not suited for use with fine masks, and may even damage the light-emitting device itself. A capping layer formed by using inorganic materials is also not usable when sputtering is used for the deposition because sputtering damages the light-emitting device.

Tris(8-hydroxyquinoline)aluminum (hereinafter, "Alq$_3$") is used as a capping layer for adjusting the refractive index (refer to Non-Patent Document 2, for example). Alq$_3$ is an organic EL material commonly used as a green-emitting material or an electron transport material, and has a weak absorption near 450 nm used for blue-emitting devices. This is problematic because it lowers the color purity of a blue-emitting device.

Another problem is that the material involves large differences in refractive indices measured in the blue, green, and red wavelength regions, preventing high coupling-out efficiency from being obtained in all of the blue-, green-, and red-emitting devices at the same time.

In order to improve the device characteristics of organic EL devices, particularly to greatly improve the coupling-out efficiency, there is a need for a capping layer material having a high refractive index that involves only small differences in refractive indices measured in the blue, green, and red wavelength regions, and that excels in thin-film stability and durability.

CITATION LIST

Patent Documents

Patent Document 1: JP-A-8-048656
Patent Document 2: Japanese Patent No. 3194657

Non-Patent Documents

Non-Patent Document 1: The Japan Society of Applied Physics, 9th lecture preprints, pp. 55 to 61 (2001)
Non-Patent Document 2: Appl. Phys. Lett., 78, 544 (2001)
Non-Patent Document 3: Appl. Phys. Lett., 82, 466 (2003)

SUMMARY OF THE INVENTION

Problems that the Invention is to Solve

An object of the present invention is to provide, in order to improve the device characteristics of organic EL devices, particularly to greatly improve the coupling-out efficiency, an organic EL device that includes a capping layer formed of a material having a high refractive index that involves only small differences in refractive indices measured in the blue, green, and red wavelength regions, and that excels in thin-film stability and durability, and does not have an absorption in the blue, green, and red wavelength region.

Some of the physical properties of the capping layer material suited for the present invention include (1) high refractive index, (2) small differences in refractive indices measured in the blue, green, and red wavelength regions, (3) vapor deposition capability and no heat decomposition, (4) stable thin-film state, and (5) high glass transition temperature. Some of the physical properties of the device suited for the present invention include (1) high coupling-out efficiency, (2) no color purity reduction, (3) no change over time for passage of light, and (4) long life.

Means for Solving the Problems

In order to achieve the foregoing object, the present inventors focused on the excellent thin-film stability and durability of phthalic acid derivatives having specific structures. Specific phthalic acid derivatives having high refractive indices were selected, and used as capping layer materials to produce organic EL devices, and the device characteristics were evaluated to complete the present invention.

Specifically, the present invention is intended to provide the following organic EL device.

1) An organic EL device including at least an anode, a hole transport layer, a light emitting layer, an electron transport layer, a cathode, and a capping layer in this order, wherein the capping layer contains a phthalic acid derivative represented by the following general formula (1).

[Chemical Formula 1]

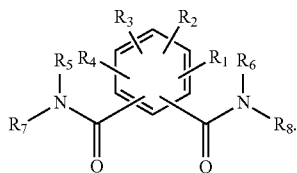

(1)

In the formula, $R_1$ to $R_4$ may be the same as or different, and represent a hydrogen atom, a deuterium atom, a fluorine atom, a chlorine atom, a bromine atom, an iodine atom, hydroxyl, cyano, trifluoromethyl, nitro, linear or branched alkyl of 1 to 8 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 8 carbon atoms that may have a substituent, cycloalkyloxy of 5 to 10 carbon atoms that may have a substituent, a substituted or unsubstituted aromatic hydrocarbon group, a substituted or unsubstituted heterocyclic group, a substituted or unsubstituted condensed polycyclic aromatic group, or substituted or unsubstituted aryloxy. $R_5$ and $R_6$ may be the same or different, and represent a hydrogen atom, a deuterium atom, linear or branched alkyl of 1 to 8 carbon atoms that may have a substituent, cycloalkyl of 5 to 10 carbon atoms that may have a substituent, linear or branched alkenyl of 2 to 6 carbon atoms that may have a substituent, a substituted or unsubstituted aromatic hydrocarbon group, a substituted or unsubstituted heterocyclic group, or a substituted or unsubstituted condensed polycyclic aromatic group. $R_7$ and $R_8$ may be the same or different, and represent cycloalkyl of 5 to 10 carbon atoms that may have a substituent. $R_1$ to $R_4$ may bind to each other between adjacent groups to form a ring.

2) The organic EL device of 1) wherein the capping layer contains a phthalic acid derivative represented by the following general formula (1').

[Chemical Formula 2]

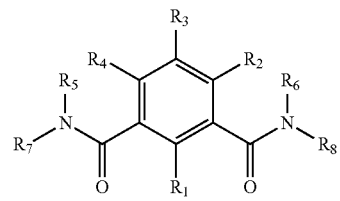

(1')

In the formula, $R_1$ to $R_4$ may be the same or different, and represent a hydrogen atom, a deuterium atom, a fluorine atom, a chlorine atom, a bromine atom, an iodine atom, hydroxyl, cyano, trifluoromethyl, nitro, linear or branched alkyl of 1 to 8 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 8 carbon atoms that may have a substituent, cycloalkyloxy of 5 to 10 carbon atoms that may have a substituent, a substituted or unsubstituted aromatic hydrocarbon group, a substituted or unsubstituted heterocyclic group, a substituted or unsubstituted condensed polycyclic aromatic group, or substituted or unsubstituted aryloxy. $R_5$ and $R_6$ may be the same or different, and represent a hydrogen atom, a deuterium atom, linear or branched alkyl of 1 to 8 carbon atoms that may have a substituent, cycloalkyl of 5 to 10 carbon atoms that may have a substituent, linear or branched alkenyl of 2 to 6 carbon atoms that may have a substituent, a substituted or unsubstituted aromatic hydrocarbon group, a substituted or unsubstituted heterocyclic group, or a substituted or unsubstituted condensed polycyclic aromatic group. $R_7$ and $R_8$ may be the same or different, and represent cycloalkyl of 5 to 10 carbon atoms that may have a substituent. $R_1$ to $R_4$ may bind to each other between adjacent groups to form a ring.

3) The organic EL device of 1), wherein the capping layer has a thickness in a range of 30 nm to 120 nm.

4) The organic EL device of 1), wherein the capping layer has a refractive index of 1.50 or more for light passing through the capping layer within the wavelength range of 400 nm to 750 nm, and has small refractive index differences in blue, green, and red wavelength regions.

5) A method for using a compound represented by the general formula (1) or (1') for the capping layer of the organic EL device.

Specific examples of the "linear or branched alkyl of 1 to 8 carbon atoms", the "cycloalkyl of 5 to 10 carbon atoms", or the "linear or branched alkenyl of 2 to 6 carbon atoms" in the "linear or branched alkyl of 1 to 8 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_4$ in general formula (1) include methyl, ethyl, n-propyl, isopropyl, n-butyl, isobutyl, tert-butyl, n-pentyl, isopentyl, neopentyl, n-hexyl, n-heptyl, isoheptyl, n-octyl, isooctyl, cyclopentyl, cyclohexyl, 1-adamantyl, 2-adamantyl, vinyl, allyl, isopropenyl, and 2-butenyl.

Specific examples of the "substituent" in the "substituted linear or branched alkyl of 1 to 8 carbon atoms", the "substituted cycloalkyl of 5 to 10 carbon atoms", or the "substituted linear or branched alkenyl of 2 to 6 carbon atoms" represented by $R_1$ to $R_4$ in general formula (1) include a deuterium atom, trifluoromethyl, cyano, nitro, or hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; linear or branched alkyloxy of 1 to 8 carbon atoms such as methyloxy, ethyloxy, and propyloxy; alkenyl such as allyl; aralkyl such as benzyl, naphthylmethyl, and phenethyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

Specific examples of the "linear or branched alkyloxy of 1 to 8 carbon atoms" or the "cycloalkyloxy of 5 to 10 carbon atoms" in the "linear or branched alkyloxy of 1 to 8 carbon atoms that may have a substituent" or the "cycloalkyloxy of 5 to 10 carbon atoms that may have a substituent" represented by $R_1$ to $R_4$ in general formula (1) include methyloxy, ethyloxy, n-propyloxy, isopropyloxy, n-butyloxy, tert-butyloxy, n-pentyloxy, n-hexyloxy, n-heptyloxy, isoheptyloxy, n-octyloxy, isooctyloxy, cyclopentyloxy, cyclohexyloxy, cycloheptyloxy, cyclooctyloxy, 1-adamantyloxy, and 2-adamantyloxy.

Specific examples of the "substituent" in the "substituted linear or branched alkyloxy of 1 to 8 carbon atoms" or the "substituted cycloalkyloxy of 5 to 10 carbon atoms" represented by $R_1$ to $R_4$ in general formula (1) include a deuterium atom, trifluoromethyl, cyano, nitro, or hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; linear or branched alkyloxy of 1 to 8 carbon atoms such as methyloxy, ethyloxy, and propyloxy; alkenyl such as allyl; aralkyl such as benzyl, naphthylmethyl, and phenethyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

Specific examples of the "aromatic hydrocarbon group", the "heterocyclic group", or the "condensed polycyclic aromatic group" in the "substituted or unsubstituted aromatic hydrocarbon group", the "substituted or unsubstituted heterocyclic group", or the "substituted or unsubstituted condensed polycyclic aromatic group" represented by $R_1$ to $R_4$ in general formula (1) include phenyl, biphenylyl, terphenylyl, naphthyl, anthracenyl, phenanthryl, fluorenyl, indenyl, pyrenyl, perylenyl, fluoranthenyl, triphenylenyl, pyridyl, furyl, pyranyl, thienyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl.

Specific examples of the "substituent" in the "substituted aromatic hydrocarbon group", the "substituted heterocyclic group", or the "substituted condensed polycyclic aromatic group" represented by $R_1$ to $R_4$ in general formula (1) include a deuterium atom, cyano, trifluoromethyl, nitro, hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; cycloalkyl of 5 to 10 carbon atoms such as cyclopentyl, and cyclohexyl; linear or branched alkenyl of 2 to 6 carbon atoms such as vinyl, allyl, 2-butenyl, and 1-hexenyl; linear or branched alkyloxy of 1 to 8 carbon atoms such as methyloxy, ethyloxy, and propyloxy; cycloalkyloxy of 5 to 10 carbon atoms such as cyclopentyloxy, and cyclohexyloxy; aralkyl such as benzyl, naphthylmethyl, and phenethyl; aryloxy such as phenyloxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

Specific examples of the "aryloxy" in the "substituted or unsubstituted aryloxy" represented by $R_1$ to $R_4$ in general formula (1) include phenyloxy, tolyloxy, biphenylyloxy, terphenylyloxy, naphthyloxy, anthryloxy, phenanthryloxy, fluorenyloxy, indenyloxy, pyrenyloxy, and perylenyloxy.

Specific examples of the "substituent" in the "substituted aryloxy" represented by $R_1$ to $R_4$ in general formula (1) include a deuterium atom, cyano, trifluoromethyl, nitro, hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; cycloalkyl of 5 to 10 carbon atoms such as cyclopentyl, and cyclohexyl; linear or branched alkenyl of 2 to 6 carbon atoms such as vinyl, allyl, 2-butenyl, and 1-hexenyl; linear or branched alkyloxy of 1 to 8 carbon atoms such as methyloxy, ethyloxy, and propyloxy; cycloalkyloxy of 5 to 10 carbon atoms such as cyclopentyloxy, and cyclohexyloxy; aralkyl such as benzyl, naphthylmethyl, and phenethyl; aryloxy such as phenyloxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

Specific examples of the "linear or branched alkyl of 1 to 8 carbon atoms", the "cycloalkyl of 5 to 10 carbon atoms", or the "linear or branched alkenyl of 2 to 6 carbon atoms" in the "linear or branched alkyl of 1 to 8 carbon atoms that may have a substituent", the "cycloalkyl of 5 to 10 carbon atoms that may have a substituent", or the "linear or branched alkenyl of 2 to 6 carbon atoms that may have a substituent" represented by $R_5$ and $R_6$ in general formula (1) include methyl, ethyl, n-propyl, isopropyl, n-butyl, isobutyl, tert-butyl, n-pentyl, isopentyl, neopentyl, n-hexyl, n-heptyl, isoheptyl, n-octyl, isooctyl, cyclopentyl, cyclohexyl, 1-adamantyl, 2-adamantyl, vinyl, allyl, isopropenyl, and 2-butenyl.

Specific examples of the "substituent" in the "substituted linear or branched alkyl of 1 to 8 carbon atoms", the "substituted cycloalkyl of 5 to 10 carbon atoms", or the "substituted linear or branched alkenyl of 2 to 6 carbon atoms" represented by $R_5$ and $R_6$ in general formula (1) include a deuterium atom, trifluoromethyl, cyano, nitro, or hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; linear or branched alkyloxy of 1 to 8 carbon atoms such as methyloxy, ethyloxy, and propyloxy; alkenyl such as allyl; aralkyl such as benzyl, naphthylmethyl, and phenethyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

Specific examples of the "aromatic hydrocarbon group", the "heterocyclic group", or the "condensed polycyclic aromatic group" in the "substituted or unsubstituted aromatic hydrocarbon group", the "substituted or unsubstituted heterocyclic group", or the "substituted or unsubstituted condensed polycyclic aromatic group" represented by $R_5$ and $R_6$ in general formula (1) include phenyl, biphenylyl, terphenylyl, naphthyl, anthracenyl, phenanthryl, fluorenyl, indenyl, pyrenyl, perylenyl, fluoranthenyl, triphenylenyl, pyridyl, furyl, pyranyl, thienyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl.

Specific examples of the "substituent" in the "substituted aromatic hydrocarbon group", the "substituted heterocyclic group", or the "substituted condensed polycyclic aromatic group" represented by $R_5$ and $R_6$ in general formula (1) include a deuterium atom, cyano, trifluoromethyl, nitro, hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; cycloalkyl of 5 to 10 carbon atoms such as cyclopentyl, and cyclohexyl; linear or branched alkenyl of 2 to 6 carbon atoms such as vinyl, allyl, 2-butenyl, and 1-hexenyl; linear or branched alkyloxy of 1 to 8 carbon atoms such as methyloxy, ethyloxy, and propyloxy; cycloalkyloxy of 5 to 10 carbon atoms such as cyclopentyloxy, and cyclohexyloxy; aralkyl such as benzyl, naphthylmethyl, and phenethyl; aryloxy such as phenyloxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

Specific examples of the "cycloalkyl of 5 to 10 carbon atoms" in the "cycloalkyl of 5 to 10 carbon atoms that may have a substituent" represented by $R_7$ and $R_8$ in general formula (1) include cyclopentyl, cyclohexyl, cycloheptyl, cyclooctyl, cyclononyl, cyclodecyl, 1-adamantyl, and 2-adamantyl.

Specific examples of the "substituent" in the "substituted cycloalkyl of 5 to 10 carbon atoms" represented by $R_7$ and $R_8$ in general formula (1) include a deuterium atom, trifluoromethyl, cyano, nitro, or hydroxyl; halogen atoms such as a fluorine atom, a chlorine atom, a bromine atom, and an iodine atom; linear or branched alkyl of 1 to 8 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, and isooctyl; linear or branched alkyloxy of 1 to 8 carbon atoms such as methyloxy, ethyloxy, and propyloxy; alkenyl such as allyl; aralkyl such as benzyl, naphthylmethyl, and phenethyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with a heterocyclic group, such as dipyridylamino, dithienylamino, and dipiperidinylamino; dialkenylamino groups such as diallylamino; and disubstituted amino groups substituted with substituents selected from alkyl, aromatic hydrocarbon groups, condensed polycyclic aromatic groups, aralkyl, heterocyclic groups, and alkenyl. These substituents may be further substituted with other substituents, and may bind to each other via a single bond, an oxygen atom, or a sulfur atom to form a ring.

The "linear or branched alkyl of 1 to 8 carbon atoms that may have a substituent" represented by $R_1$ to $R_4$ in general formula (1) is preferably a "linear or branched alkyl of 1 to 4 carbon atoms that may have a substituent", particularly preferably tert-butyl.

The "cycloalkyl of 5 to 10 carbon atoms that may have a substituent" represented by $R_1$ to $R_4$ in general formula (1) is preferably a "cycloalkyl of 5 to 6 carbon atoms that may have a substituent".

The "linear or branched alkenyl of 2 to 6 carbon atoms that may have a substituent" represented by $R_1$ to $R_4$ in general formula (1) is preferably a "linear or branched alkenyl of 2 to 4 carbon atoms that may have a substituent".

The "linear or branched alkyloxy of 1 to 8 carbon atoms that may have a substituent" represented by $R_1$ to $R_4$ in general formula (1) is preferably a "linear or branched alkyloxy of 1 to 4 carbon atoms that may have a substituent".

The "cycloalkyloxy of 5 to 10 carbon atoms that may have a substituent" represented by $R_1$ to $R_4$ in general formula (1) is preferably a "cycloalkyloxy of 5 to 6 carbon atoms that may have a substituent".

$R_5$ and $R_6$ in general formula (1) are preferably hydrogen atoms or deuterium atoms, particularly preferably hydrogen atoms.

The "cycloalkyl of 5 to 10 carbon atoms that may have a substituent" represented by $R_5$ and $R_6$ in general formula (1) is preferably 1-adamantyl, or 2-adamantyl, particularly preferably cyclopentyl, cyclohexyl, cycloheptyl, or 4-tert-butyl-cyclohexyl.

The phthalic acid derivatives represented by the general formula (1) used in the organic EL device of the present invention may be used as the constituent material of the capping layer of the organic EL device.

In the organic EL device of the present invention, the thickness of the capping layer ranges from preferably 30 nm to 120 nm, more preferably 40 nm to 80 nm.

In the organic EL device of the present invention, the capping layer has a refractive index of preferably 1.50 or more, more preferably 1.55 or more, particularly preferably 1.60 or more for light passing through the capping layer within the wavelength range of 400 nm to 750 nm.

In the organic EL device of the present invention, the differences in the refractive indices of the capping layer for light passing through the capping layer within the wavelength range of 400 nm to 750 nm as measured in the blue, green, and red wavelength regions are preferably 0.04 or less for $\Delta_{B-G}$ (the difference in the refractive indices measured in a blue region (B: 450 nm) and a green region (G: 520 nm), 0.04 or less for $\Delta_{G-R}$ (the difference in the refractive indices measured in a green region (G: 520 nm) and a red region (R: 630 nm), and 0.07 or less for $\Delta_{B-R}$ (the difference in the refractive indices measured in a blue region (B: 450 nm) and a red region (R: 630 nm), more preferably 0.02 or less for $\Delta_{B-G}$, 0.02 or less for $\Delta_{G-R}$, and 0.03 or less for $\Delta_{B-R}$.

In the organic EL device of the present invention, the capping layer may be produced by laminating two or more different constituent materials.

Advantage of the Invention

In the organic EL device of the present invention, a capping layer having a higher refractive index than the semi-transparent electrode is provided on the outer side of the transparent or semi-transparent electrode. This can greatly improve the coupling-out efficiency of the organic EL device. The capping layer uses the phthalic acid derivatives represented by the general formula (1) of the present invention, and can be deposited at temperatures of 400° C. or less. This makes it possible to easily optimize the coupling-out efficiency of each color over the same thickness with the use of a fine mask, without damaging the light-emitting device, the organic EL device can be suitably applied to a full-color display, and clear and bright images can be displayed with high color purity.

The capping layer material used in the organic EL device of the present invention is a material for organic EL devices. The capping layer material has a high refractive index, and involves only small differences in refractive indices measured in the blue, green, and red wavelength regions, and excels in thin-film stability and durability. This can greatly improve coupling-out efficiency compared to conventional organic EL devices. The invention also has made it possible to realize a high-efficiency, long-life organic EL device.

BRIEF DESCRIPTION OF THE DRAWINGS

FIG. 1 is a diagram representing the configuration of the organic EL devices of Example 10 and Comparative Example 1.

MODE FOR CARRYING OUT THE INVENTION

The phthalic acid derivatives represented by the general formula (1) preferably used in the organic EL device of the present invention may be synthesized by using known methods. For example, the isophthalic acid derivatives used in the present invention may be synthesized through a reaction of a dichloride of a corresponding isophthalic acid and an alicyclic hydrocarbon having a corresponding amino group in the presence of a base or the like. Another possible synthesis method is a reaction between a corresponding isophthalic acid and an alicyclic hydrocarbon having a corresponding amino group in the presence of a dehydration-condensation agent.

The following presents specific examples of particularly preferred compounds among the phthalic acid derivatives of the general formula (1) preferably used in the organic EL device of the present invention. The present invention, however, is not limited to these compounds.

Hydrogen atoms are omitted in the following structural formulae.

The following structural formulae only show two-dimensional forms of the formulae, even if stereoisomers thereof may exist.

[Chemical Formula 3]

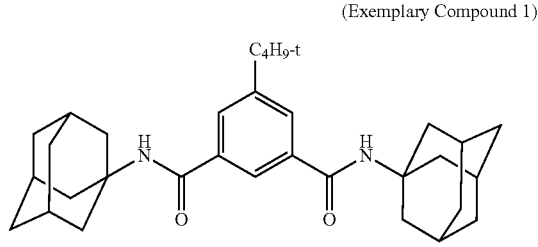

(Exemplary Compound 1)

[Chemical Formula 4]

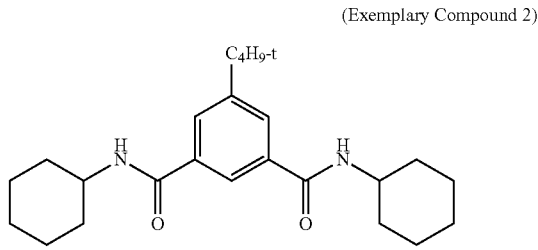

(Exemplary Compound 2)

[Chemical Formula 5]

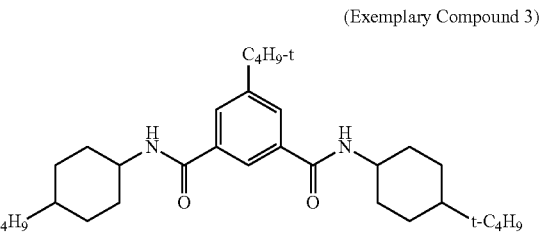

(Exemplary Compound 3)

[Chemical Formula 6]

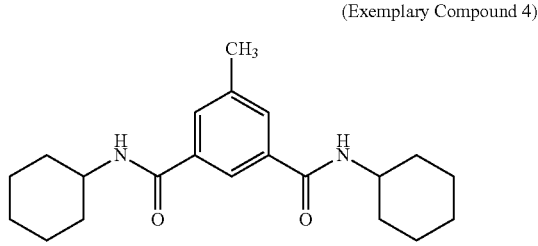

(Exemplary Compound 4)

-continued

[Chemical Formula 7]

(Exemplary Compound 5)
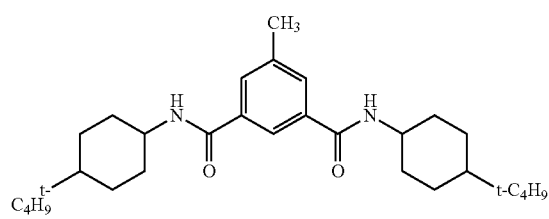

[Chemical Formula 8]

(Exemplary Compound 6)
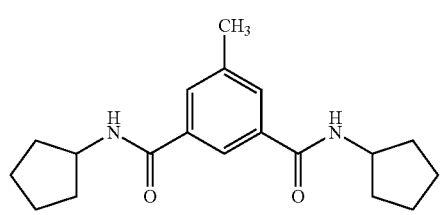

[Chemical Formula 9]

(Exemplary Compound 7)
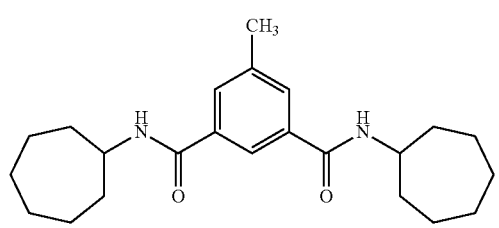

[Chemical Formula 10]

(Exemplary Compound 8)
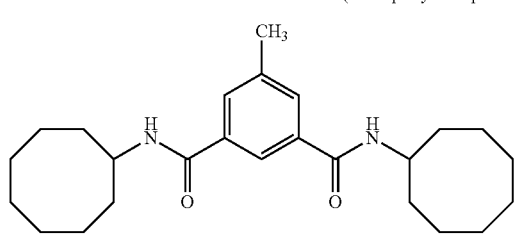

[Chemical Formula 11]

(Exemplary Compound 9)
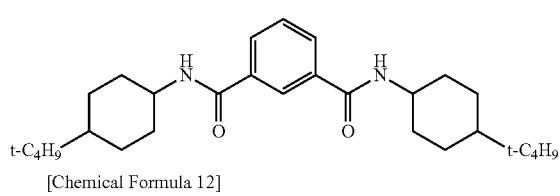

[Chemical Formula 12]

(Exemplary Compound 10)
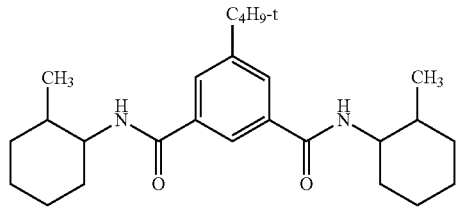

-continued

[Chemical Formula 13]

(Exemplary Compound 11)
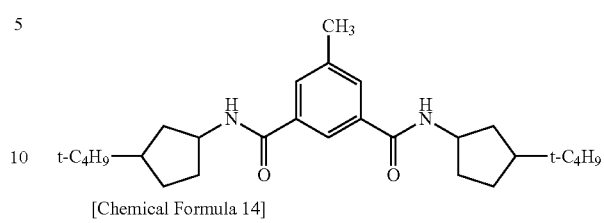

[Chemical Formula 14]

(Exemplary Compound 12)
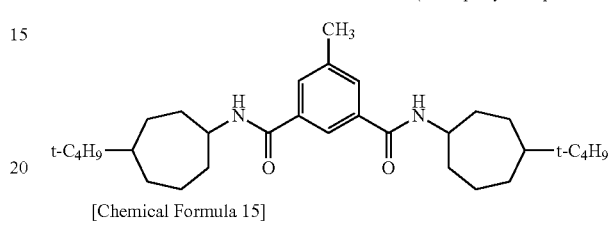

[Chemical Formula 15]

(Exemplary Compound 13)
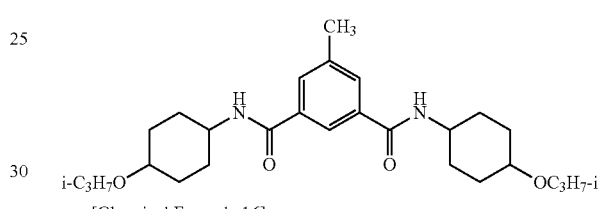

[Chemical Formula 16]

(Exemplary Compound 14)
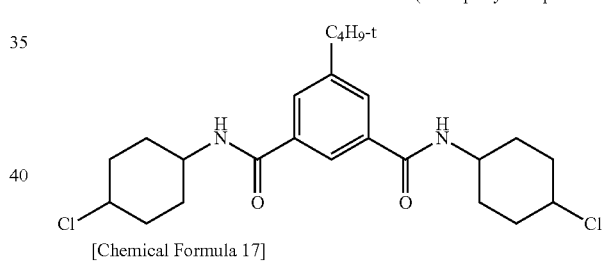

[Chemical Formula 17]

(Exemplary Compound 15)
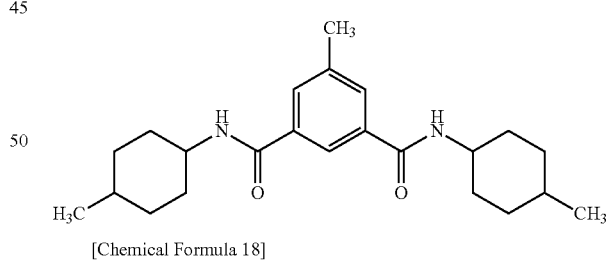

[Chemical Formula 18]

(Exemplary Compound 16)
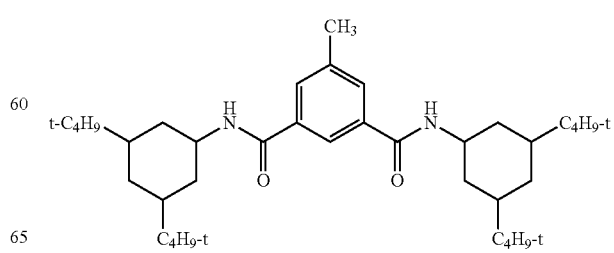

-continued

[Chemical Formula 19]

(Exemplary Compound 17)

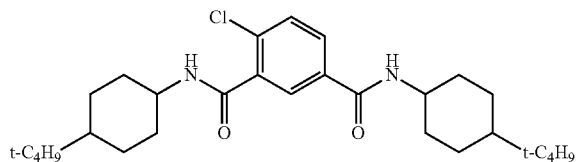

[Chemical Formula 20]

(Exemplary Compound 18)

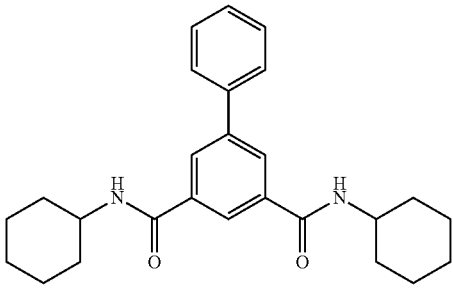

[Chemical Formula 21]

(Exemplary Compound 19)

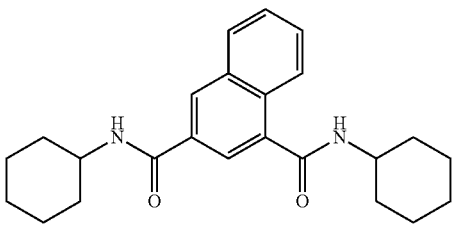

[Chemical Formula 22]

(Exemplary Compound 20)

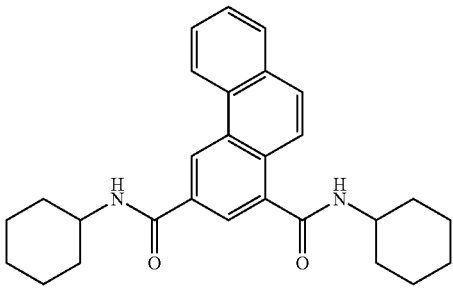

These compounds were purified by methods such as column chromatography, adsorption using, for example, a silica gel, activated carbon, or activated clay, and recrystallization or crystallization using a solvent, and finally by methods such as sublimation. The compounds were identified by using methods such as NMR analysis. Melting point, glass transition point (Tg), and refractive index were taken for the measurement of physical properties. The melting point can be used as an index of ease of vapor deposition, the glass transition point (Tg) as an index of stability in the thin-film state, and the refractive index as an index of improvement of coupling-out efficiency.

Melting point and glass transition point (Tg) were measured by using a powder, using a high-sensitive differential scanning calorimeter (DSC3100S produced by Bruker AXS).

For the measurement of refractive index, a 60 nm-thick thin film was fabricated on a silicon substrate, and a high-speed spectroscopic ellipsometer (Model M-2000 produced by J. A. Woollam) was used.

The organic EL device of the present invention may be a light-emitting device of a top-emission structure that includes a metal anode, a hole transport layer, a light emitting layer, an electron transport layer, a semi-transparent cathode, and a capping layer successively formed on a glass substrate, optionally with a hole injection layer between the anode and the hole transport layer, an electron blocking layer between the hole transport layer and the light emitting layer, a hole blocking layer between the light emitting layer and the electron transport layer, or an electron injection layer between the electron transport layer and the cathode. Some of the organic layers in the multilayer structure may be omitted, or may serve more than one function. For example, a single organic layer may serve as the hole transport layer and the electron blocking layer, or as the electron transport layer and the hole blocking layer. The total thickness of the layers in the organic EL device is preferably about 200 nm to 750 nm, more preferably about 350 nm to 600 nm. The thickness of the capping layer is, for example, preferably 30 nm to 120 nm, more preferably 40 nm to 80 nm. In this way, a desirable coupling-out efficiency can be obtained. The thickness of the capping layer may appropriately vary according to such factors as the type of the light-emitting material used for the light-emitting device, and the thicknesses of the organic EL device other than the capping layer.

Electrode materials with a large work function, such as ITO and gold, are used as the anode of the organic EL device of the present invention.

The hole injection layer of the organic EL device of the present invention may be made of various materials, including arylamine compounds of a structure in which three or more triphenylamine structures are joined to each other within the molecule via a single bond or via a divalent group that does not contain a heteroatom, for example, such as starburst-type triphenylamine derivatives, and triphenylamine tetramers and other such materials; porphyrin compounds as represented by copper phthalocyanine; accepting heterocyclic compounds such as hexacyano azatriphenylene; and coating-type polymer materials. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin film by using a vapor deposition method, or other known methods such as spin coating and an inkjet method.

Preferred examples of the material used for the hole transport layer of the organic EL device of the present invention include N,N'-diphenyl-N,N'-di(m-tolyl)benzidine (hereinafter, referred to simply as TPD), N,N'-diphenyl-N,N'-di(α-naphthyl)benzidine (hereinafter, referred to simply as NPD), and 1,1-bis[4-(di-4-tolylamino)phenyl]cyclohexane (hereinafter, referred to simply as TAPC), particularly arylamine compounds of a structure in which two triphenylamine structures are joined to each other within the molecule via a single bond or via a divalent group that does not contain a heteroatom, for example, N,N,N',N'-tetrabiphenylylbenzidine. It is also preferable to use arylamine compounds of a structure in which three or more triphenylamine structures are joined to each other within the molecule via a single bond or via a divalent group that does not contain a heteroatom, for example, various triphenylamine trimers and tetramers. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin film by using a vapor deposition method, or other known methods such as spin coating and an inkjet method.

Further, in the hole injection layer or the hole transport layer, those obtained by the P-doping of material such as trisbromophenylamine hexachloroantimony in the material commonly used for these layers may be used. Further, for example, polymer compounds having a TPD structure as a part of the compound structure also may be used.

Examples of the material used for the electron blocking layer of the organic EL device of the present invention include compounds having an electron blocking effect, including, for example, carbazole derivatives such as 4,4',4''-tri(N-carbazolyl)triphenylamine (hereinafter, referred to simply as "TCTA"), 9,9-bis[4-(carbazol-9-yl)phenyl]fluorene, 1,3-bis(carbazol-9-yl)benzene (hereinafter, referred to simply as "mCP"), and 2,2-bis(4-carbazol-9-ylphenyl)adamantane (hereinafter, referred to simply as "Ad-Cz"); and compounds having a triphenylsilyl group and a triarylamine structure, as represented by 9-[4-(carbazol-9-yl)phenyl]-9-[4-(triphenylsilyl)phenyl]-9H-fluorene. These may be deposited alone, or may be used as a single layer deposited as a mixture with other materials, or as a laminate of individually deposited layers, a laminate of a layer deposited as a mixture, or a laminate of a layer deposited alone and a layer deposited as a mixture. These materials may be formed into a thin-film by using a vapor deposition method, or other known methods such as spin coating and an inkjet method.

Examples of the material used for the light emitting layer of the organic EL device of the present invention include quinolinol derivative metal complexes such as $Alq_3$, various metal complexes, anthracene derivatives, bis(styryl)benzene derivatives, pyrene derivatives, oxazole derivatives, and polyparaphenylene vinylene derivatives. Further, the light emitting layer may be configured from a host material and a dopant material. Examples of the host material include thiazole derivatives, benzimidazole derivatives, and polydialkyl fluorene derivatives, in addition to the foregoing light-emitting materials. Examples of the dopant material include quinacridone, coumalin, rubrene, perylene, derivatives thereof, benzopyran derivatives, rhodamine derivatives, and aminostyryl derivatives. These may be deposited alone, or may be used as a single layer deposited as a mixture with other materials, or as a laminate of individually deposited layers, a laminate of layers deposited as a mixture, or a laminate of a layer deposited alone and a layer deposited as a mixture.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as $Ir(ppy)_3$, blue phosphorescent materials such as FIrpic and FIr6, and red phosphorescent materials such as $Btp_2Ir(acac)$. Here, carbazole derivatives such as 4,4'-di(N-carbazolyl)biphenyl (hereinafter, referred to simply as "CBP"), TCTA, and mCP may be used as the hole injecting and transporting host material. Compounds such as p-bis(triphenylsilyl)benzene (hereinafter, referred to simply as "UGH2"), and 2,2',2''-(1,3,5-phenylene)-tris(1-phenyl-1H-benzimidazole) (hereinafter, referred to simply as "TPBI") may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

These materials may be formed into a thin-film by using a vapor deposition method, or other known methods such as spin coating and an inkjet method.

The hole blocking layer of the organic EL device of the present invention may be formed by using various hole blocking compounds, including phenanthroline derivatives such as bathocuproin (hereinafter, referred to simply as BCP), metal complexes of quinolinol derivatives such as aluminum(III)bis(2-methyl-8-quinolinate)-4-phenylphenolate (hereinafter, referred to simply as BAlq), various rare earth complexes, triazole derivatives, triazine derivatives, and oxadiazole derivatives. These materials may also serve as the material of the electron transport layer. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin-film by using a vapor deposition method, or other known methods such as spin coating and an inkjet method.

Examples of the material used for the electron transport layer of the organic EL device of the present invention include metal complexes of quinolinol derivatives such as $Alq_3$, and BAlq, various metal complexes, triazole derivatives, triazine derivatives, oxadiazole derivatives, thiadiazole derivatives, pyridoindole derivatives, carbodiimide derivatives, quinoxaline derivatives, phenanthroline derivatives, and silole derivatives. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin-film by using a vapor deposition method, or other known methods such as spin coating and an inkjet method.

Examples of the material used for the electron injection layer of the organic EL device of the present invention include alkali metal salts (such as lithium fluoride, and cesium fluoride), alkaline earth metal salts (such as magnesium fluoride), and metal oxides (such as aluminum oxide). However, the electron injection layer may be omitted upon preferably selecting the electron transport layer and the cathode.

The electron injection layer or the electron transport layer may be one obtained by the N-doping of metals such as cesium in the materials commonly used for these layers.

The semi-transparent cathode of the organic EL device of the present invention may be made of an electrode material having a low work function (such as aluminum), or an alloy of an electrode material having an even lower work function (such as a magnesium-silver alloy, a magnesium-calcium alloy, a magnesium-indium alloy, and an aluminum-magnesium alloy), or ITO or IZO.

Preferred for use as the capping layer of the organic EL device of the present invention is, for example, the phthalic acid derivatives represented by the general formula (1), and arylamine compounds of a structure in which two triphenylamine structures are joined to each other within the molecule via a single bond or via a divalent group that does not contain a heteroatom, for example, N,N,N',N'-tetrabiphenylylbenzidine. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin-film by using a vapor deposition method, or other known methods such as spin coating and an inkjet method.

The organic EL device shown in FIG. 1 is described as an organic EL device of a top-emission structure. However, the present invention is not limited to this, and is also applicable to an organic EL device of a bottom-emission structure, and an organic EL device of a dual-emission structure in which light is emitted in two directions from the top and the bottom. In these cases, the electrodes disposed on the light emerging side of the light-emitting device need to be transparent or semi-transparent.

The refractive index of the material forming the capping layer is preferably larger than the refractive index of the adjacent electrode. Specifically, the capping layer improves the coupling-out efficiency of the organic EL device, and the effect becomes more prominent as the reflectance at the interface between the capping layer and the material in contact with the capping layer increases, and increases the light interference effect. The material forming the capping layer thus preferably has a larger refractive index than the adjacent electrode, and the refractive index is preferably 1.50 or more, more preferably 1.55 or more, particularly preferably 1.60 or more. The differences in the refractive indices of the material forming the capping layer as measured in the blue, green, and red wavelength regions are preferably 0.04 or less for $\Delta_{B-G}$ (the difference in the refractive indices measured in a blue region (B: 450 nm) and a green region (G: 520 nm)), 0.04 or less for $\Delta_{G-R}$ (the difference in the refractive indices measured in a green region (G: 520 nm) and a red region (R: 630 nm)), and 0.07 or less for $\Delta_{B-R}$ (the difference in the refractive indices measured in a blue region (B: 450 nm) and a red region (R: 630 nm)), more preferably 0.02 or less for $\Delta_{B-G}$, 0.02 or less for $\Delta_{G-R}$, and 0.03 or less for $\Delta_{B-R}$.

Example 1

The following describes the embodiment of the present invention in more detail using Examples. The present invention, however, is not limited to the following Examples. In the following, "parts" means "parts by mass" in all occurrences.

Synthesis Example 1

Synthesis of Exemplary Compound 1

Adamantylamine hydrochloride (7.6 g, 40.5 mM), triethylamine (8.2 g, 81.0 mM), and dioxane (150 ml) were added to a nitrogen-substituted reaction vessel. A dioxane solution (50 ml) of 5-tert-butyl isophthalic acid dichloride (5.0 g, 19.3 mM) was dropped into the vessel while stirring the mixture. The mixture was heated, and stirred at 65° C. for 8 hours. After being allowed to stand overnight, the reaction mixture was added to dilute hydrochloric acid (500 ml) while stirring the mixture. The precipitated crude product was collected by filtration, washed twice with water, and dispersed and washed with methanol twice. The product was dried at 60° C. under reduced pressure to obtain white crystals (9.0 g; yield 96.1%).

The structure of the obtained white crystals was identified by NMR.

$^1$H-NMR (DMSO-$d_6$) detected 44 hydrogen signals, as follows.

δ (ppm)=7.68-7.90 (5H), 2.09 (18H), 1.67 (12H), 1.32 (9H)

Example 2

Synthesis Example 2

Synthesis of Exemplary Compound 2

Cyclohexylamine (12.6 g, 127 mM), triethylamine (13.4 g, 132 mM), and dioxane (300 ml) were added to a nitrogen-substituted reaction vessel. A dioxane solution (70 ml) of 4-tert-butylisophthalic acid dichloride (15.5 g, 60 mM) was dropped into the vessel while stirring the mixture, and the mixture was further stirred for 7 hours. After being allowed to stand overnight, the reaction mixture was added to water (1000 ml) while stirring the mixture. Hydrochloric acid was added until the solution pH was 3, and the mixture was stirred for 1 hour. The precipitated crude product was collected by filtration, water-washed, and dried at 60° C. under reduced pressure to obtain white crystals (22.3 g; yield 96.6%).

The structure of the obtained white crystals was identified by NMR.

$^1$H-NMR (DMSO-$d_6$) detected 36 hydrogen signals, as follows.

δ (ppm)=8.01 (1H), 7.89-7.91 (4H), 3.76-3.81 (2H), 1.85-1.87 (4H), 1.75-1.76 (4H), 1.61-1.63 (2H), 1.29-1.41 (17H), 1.16-1.20 (2H).

Example 3

Synthesis Example 3

Synthesis of Exemplary Compound 3

4-tert-Butylcyclohexylamine (10.5 g, 67.9 mM), triethylamine (6.9 g, 67.9 mM), and dioxane (150 ml) were added to a nitrogen-substituted reaction vessel. A dioxane solution (50 ml) of 5-tert-butylisophthalic acid dichloride (8.0 g, 30.9 mM) was dropped into the vessel while stirring the mixture, and the mixture was further stirred for 7 hours. After being allowed to stand overnight, the reaction mixture was added to water (500 ml) while stirring the mixture. Hydrochloric acid was added until the solution pH was 3, and the mixture was further stirred for 1 hour. The precipitated crude product was collected by filtration, water-washed, and dried at 60° C. under reduced pressure to obtain white crystals (14.0 g; yield 91.3%) as a stereoisomer mixture.

The structure of the obtained white crystals was identified by NMR.

$^1$H-NMR (DMSO-$d_6$) detected 52 hydrogen signals, as follows.

δ (ppm)=7.82-8.12 (5H), 3.71-4.03 (2H), 0.86-1.97 (45H).

Example 4

Synthesis Example 4

Synthesis of Exemplary Compound 4

Cyclohexylamine (7.0 g, 71.0 mM), triethylamine (7.2 g, 71.0 mM), and dioxane (150 ml) were added to a nitrogen-substituted reaction vessel. A dioxane solution (50 ml) of 4-methylisophthalic acid dichloride (7.0 g, 32.3 mM) was dropped into the vessel while stirring the mixture, and the mixture was further stirred for 8 hours. After being allowed to stand overnight, the reaction mixture was added to water (500 ml) while stirring the mixture. Hydrochloric acid was added until the solution pH was 3, and the mixture was further stirred for 1 hour. The precipitated crude product was collected by filtration, water-washed, and dried at 60° C. under reduced pressure to obtain white crystals (10.6 g; yield 96.3%).

The structure of the obtained white crystals was identified by NMR.

$^1$H-NMR (DMSO-d$_6$) detected 30 hydrogen signals, as follows.

δ (ppm)=7.71-7.98 (5H), 3.57-3.77 (2H), 2.39 (3H), 1.60-1.84 (10H), 1.16-1.1.35 (10H).

Example 5

Synthesis Example 5

Synthesis of Exemplary Compound 5

4-tert-Butylcyclohexylamine (11.0 g, 71.0 mM), triethylamine (7.2 g, 71.0 mM), and dioxane (150 ml) were added to a nitrogen-substituted reaction vessel. A dioxane solution (100 ml) of 4-methylisophthalic acid dichloride (7.0 g, 32.3 mM) was dropped into the vessel while stirring the mixture, and the mixture was further stirred for 3 hours. After being allowed to stand overnight, the reaction mixture was added to water (500 ml) while stirring the mixture. Hydrochloric acid was added until the solution pH was 3, and the mixture was further stirred for 1 hour. The precipitated crude product was collected by filtration, water-washed, and dried at 60° C. under reduced pressure to obtain white crystals (14.1 g; yield 96.1%) as a stereoisomer mixture.

The structure of the obtained white crystals was identified by NMR.

$^1$H-NMR (DMSO-d$_6$) detected 46 hydrogen signals, as follows.

δ (ppm)=7.55-7.97 (5H), 3.69-4.07 (2H), 0.86-2.40 (39H).

Example 6

Synthesis Example 6

Synthesis of Exemplary Compound 6

Cyclopentylamine (6.0 g, 71.0 mM), triethylamine (7.2 g, 71.0 mM), and dioxane (150 ml) were added to a nitrogen-substituted reaction vessel. A dioxane solution (50 ml) of 4-methylisophthalic acid dichloride (7.0 g, 32.3 mM) was dropped into the vessel while stirring the mixture, and the mixture was further stirred for 5 hours. After being allowed to stand overnight, the reaction mixture was added to water (500 ml) while stirring the mixture. Hydrochloric acid was added until the solution pH was 3, and the mixture was further stirred for 1 hour. The precipitated crude product was collected by filtration, water-washed, and dried at 60° C. under reduced pressure to obtain white crystals (9.5 g; yield 94.2%).

The structure of the obtained white crystals was identified by NMR.

$^1$H-NMR (DMSO-d$_6$) detected 26 hydrogen signals, as follows.

δ (ppm)=8.33-8.34 (2H), 8.04 (1H), 7.75 (2H), 4.42-4.24 (2H), 2.39 (3H), 1.89 (4H), 1.70 (4H), 1.53-1.55 (8H).

Example 7

Synthesis Example 7

Synthesis of Exemplary Compound 7

Cycloheptylamine (8.0 g, 71.0 mM), triethylamine (7.2 g, 71.0 mM), and dioxane (150 ml) were added to a nitrogen-substituted reaction vessel. A dioxane solution (50 ml) of 4-methylisophthalic acid dichloride (7.0 g, 32.3 mM) was dropped into the vessel while stirring the mixture, and the mixture was further stirred for 2.5 hours. After being allowed to stand overnight, the reaction mixture was added to water (500 ml) while stirring the mixture. Hydrochloric acid was added until the solution pH was 3, and the mixture was further stirred for 1 hour. The precipitated crude product was collected by filtration, water-washed, and dried at 60° C. under reduced pressure to obtain white crystals (11.6 g; yield 96.4%).

The structure of the obtained white crystals was identified by NMR.

$^1$H-NMR (DMSO-d$_6$) detected 34 hydrogen signals, as follows.

δ (ppm)=7.96 (1H), 7.81 (2H), 7.70 (2H), 3.97 (2H), 2.38 (3H), 1.47-1.87 (24H).

Example 8

The melting point and the glass transition point of the compound of the present invention were determined using a high-sensitive differential scanning calorimeter (DSC 3100S produced by Bruker AXS).

| | | Exemplary Compound 1 |
|---|---|---|
| Melting point | Glass transition point | |
| 243° C. | 153° C. | |

The compound of the present invention was shown to have a glass transition point of 100° C. or more. This indicates that the compound of the present invention has a stable thin-film state.

Example 9

The compound (Exemplary Compound 1) of the present invention was used to produce a vapor-deposited film (thickness 60 nm) on a silicon substrate, and the refractive indices in the blue (B: 450 nm), green (G: 520 nm), and red (R: 630 nm) wavelength regions were measured with a high-speed spectroscopic ellipsometer (Model M-2000 produced by J. A. Woollam). The measurement results are summarized in Table 1. These refractive index values were used to calculate refractive index differences in the wavelength regions of the different colors ($\Delta_{B-G}$: a difference in the refractive indices measured in the blue region (B: 450 nm) and the green region (G: 520 nm), $\Delta_{G-R}$: a difference in the refractive indices measured in the green region (G: 520 nm) and the red region (R: 630 nm), $\Delta_{B-R}$: a difference in the refractive indices measured in the blue region (B: 450 nm) and the red region (R: 630 nm)). The results are summarized in Table 2.

Comparative Example 1

The refractive index measurements were performed in the same manner as in Example 9, except that Exemplary Compound was replaced with Alg$_3$. The measurement results are summarized in Table 1. The refractive index differences in the wavelength regions of the different colors ($\Delta_{B-G}$, $\Delta_{G-R}$, $\Delta_{B-R}$) were also calculated. The results are summarized in Table 2.

Comparative Example 2

The refractive index measurements were performed in the same manner as in Example 9, except that Exemplary Compound was replaced with NPD. The measurement results are summarized in Table 1. The refractive index differences in the wavelength regions of the different colors ($\Delta_{B-G}$, $\Delta_{G-R}$, $\Delta_{B-R}$) were also calculated. The results are summarized in Table 2.

TABLE 1

|  | Refractive index | | |
| --- | --- | --- | --- |
|  | B: 450 nm | G: 520 nm | R: 630 nm |
| Exemplary compound 1 | 1.57 | 1.56 | 1.55 |
| Alq$_3$ | 1.84 | 1.78 | 1.7 |
| NPD | 1.93 | 1.84 | 1.79 |

TABLE 2

|  | $\Delta_{B-G}$ | $\Delta_{G-R}$ | $\Delta_{B-R}$ |
| --- | --- | --- | --- |
| Exemplary compound 1 | 0.01 | 0.01 | 0.02 |
| Alq$_3$ | 0.06 | 0.08 | 0.14 |
| NPD | 0.09 | 0.05 | 0.14 |

As demonstrated above, the compound of the present invention has high refractive indices, and the refractive index differences in the blue, green, and red wavelength regions were all 0.04 or less, considerably smaller than the refractive index differences (0.06 to 0.14) of Alq$_3$, and the refractive index differences (0.05 to 0.14) of NPD. This result indicates that the problem of low coupling-out efficiency in all the blue, green, and red wavelength regions can be alleviated, and that the coupling-out efficiency of each color can be optimized more easily over the same thickness in the organic EL device.

Example 10

An organic EL device was fabricated by successively vapor depositing a hole injection layer 3, a hole transport layer 4, a light emitting layer 5, an electron transport layer 6, an electron injection layer 7, a cathode 8, and a capping layer 9 on a glass substrate 1 that had been provided beforehand with a reflective ITO electrode as a metal anode 2 (see FIG. 1).

Specifically, the glass substrate 1 having ITO (thickness 150 nm) formed thereon was subjected to ultrasonic washing in isopropyl alcohol for 20 minutes, and dried for 10 minutes on a hot plate that had been heated to 250° C. After being subjected to a UV ozone treatment for 2 minutes, the glass substrate with ITO was installed in a vacuum vapor deposition apparatus, and the pressure was reduced to 0.001 Pa or less. This was followed by formation of the hole injection layer 3 by depositing the compound 1 of the structural formula below over the metal anode 2 in a thickness of 60 nm at a deposition rate of 6 nm/min. The hole transport layer 4 was then formed on the hole injection layer 3 by forming the compound 2 of the structural formula below in a thickness of 40 nm at a deposition rate of 6 nm/min. Then, the light emitting layer 5 was formed on the hole transport layer 4 in a thickness of 30 nm by the dual vapor deposition of the compounds 3 and 4 of the structural formulae below at a ratio of deposition rate of 5:95 in terms of compound 3: compound 4. Then, the electron transport layer 6 was formed on the light emitting layer 5 by forming the compound 5 of the structural formula below in a thickness of 30 nm at a deposition rate of 6 nm/min. The electron injection layer 7 was then formed on the electron transport layer 6 by forming lithium fluoride in a thickness of 0.5 nm at a deposition rate of 0.6 nm/min. The cathode 8 was then formed on the electron injection layer 7 by forming a magnesium-silver alloy in a thickness of 10 nm. Finally, the capping layer 9 was formed by depositing the exemplary compound 1 in a thickness of 60 nm at a deposition rate of 6 nm/min. The characteristics of the organic EL device thus fabricated were measured in the atmosphere at ordinary temperature.

Table 3 summarizes the results of the emission characteristics measurements performed by applying a DC voltage to the organic EL device.

[Chemical Formula 23]

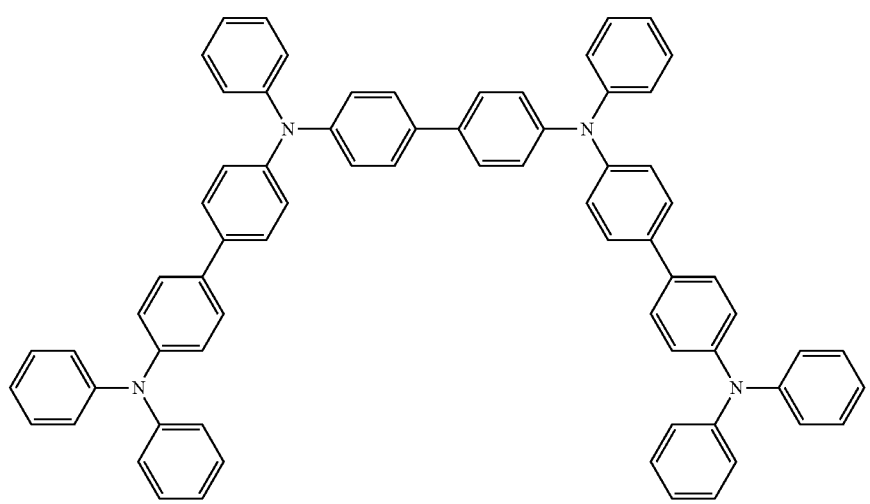

(Compound 1)

[Chemical Formula 24]
(Compound 2)
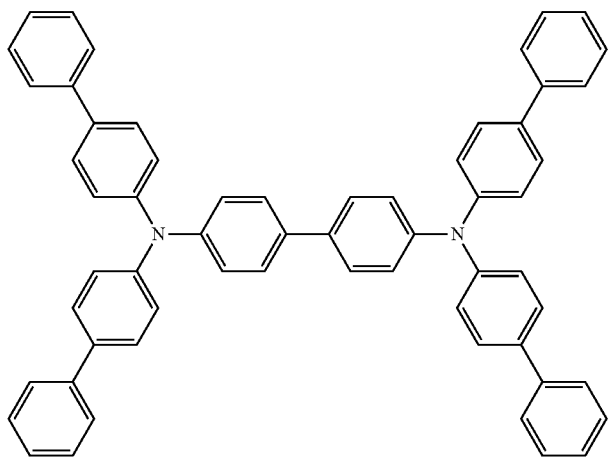
[Chemical Formula 25]
(Compound 3)
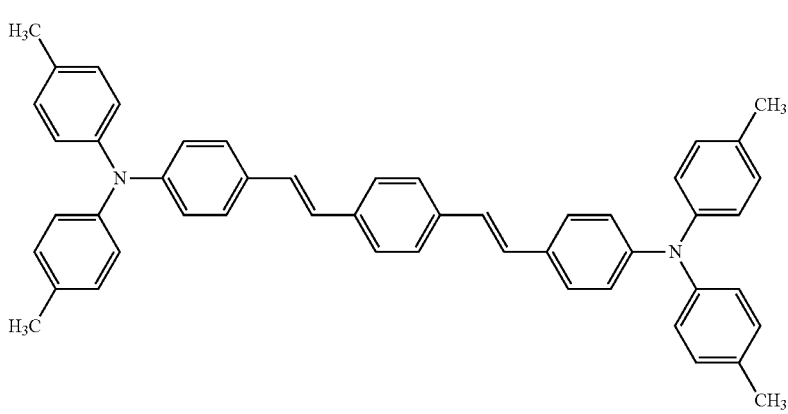
[Chemical Formula 26]
(Compound 4)
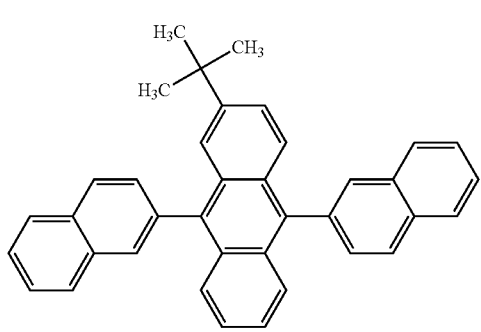

[Chemical Formula 27]

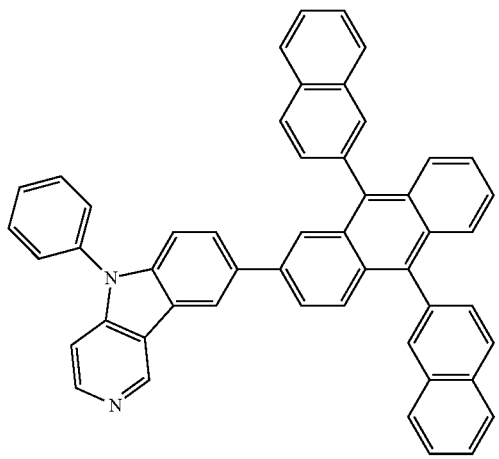

(Compound 5)

Comparative Example 3

An organic EL device was fabricated in the same manner as in Example 10, except that the capping layer 9 was formed by forming Alq$_3$ in a thickness of 60 nm, instead of using the exemplary compound 1. The characteristics of the organic EL device thus fabricated were measured in the atmosphere at ordinary temperature.

Table 3 summarizes the results of the emission characteristics measurements performed by applying a DC voltage to the organic EL device.

TABLE 3

|  |  | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) | Coupling-out efficiency (@10 mA/cm$^2$) |
|---|---|---|---|---|---|---|
| Ex. 10 | Exemplary compound 1 | 4.18 | 508 | 5.08 | 3.81 | 1.03 |
| Com. Ex. 3 | Alq$_3$ | 4.15 | 496 | 4.96 | 3.75 | 1.00 |

As shown in Table 3, the coupling-out efficiency was 3% higher in Example 10 than in Comparative Example 3 in which Alq$_3$ was used. The driving voltage, luminance, current efficiency, and power efficiency at the current density of 10 mA/cm$^2$ were all comparable to those of Comparative Example 3 in which Alq$_3$ was used.

These results indicate that the coupling-out efficiency can greatly improve when the capping layer contains the high-refractive-index material preferably used for the organic EL device of the present invention. Further, the small refractive index differences in the blue, green, and red wavelength regions improve the coupling-out efficiency in all the blue, green, and red wavelength regions.

INDUSTRIAL APPLICABILITY

As described above, the phthalic acid derivatives represented by general formula (1) preferably used for the organic EL device of the present invention have high refractive indices, and can greatly improve the coupling-out efficiency. This, combined with the stable thin-film state, makes the phthalic acid derivatives desirable compounds for organic EL devices. An organic EL device fabricated with such compounds can have high efficiency, and improved durability. The compound having no absorption in the blue, green, or red wavelength region is particularly preferred for displaying clear and bright images with high color purity. There are potential applications for, for example, home electronic appliances and illuminations.

DESCRIPTION OF REFERENCE NUMERALS AND SIGNS

1 Glass substrate
2 Metal anode
3 Hole injection layer
4 Hole transport layer
5 Light emitting layer
6 Electron transport layer
7 Electron injection layer
8 Cathode
9 Capping layer

The invention claimed is:
1. An organic electroluminescent device comprising an anode, a hole transport layer, a light emitting layer, an electron transport layer, a cathode, and a capping layer in this order, wherein the capping layer contains a phthalic acid derivative represented by the following general formula (1')

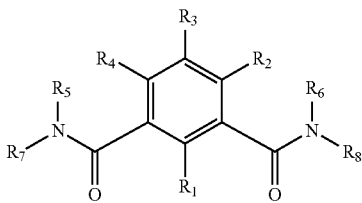

wherein $R_1$ represents a hydrogen atom or a deuterium atom;
$R_2$ represents a hydrogen atom or a deuterium atom;
$R_3$ represents a hydrogen atom, a deuterium atom, a linear or branched alkyl of 1 to 8 carbon atoms or a substituted or unsubstituted aromatic hydrocarbon group;
$R_4$ represents a hydrogen atom, a deuterium atom, a fluorine atom, a chlorine atom, a bromine atom, or an iodine atom;
$R_5$ and $R_6$ may be the same or different, and represent a hydrogen atom or a deuterium atom; and
$R_7$ and $R_8$ may be the same or different, and represent cycloalkyl of 5 to 10 carbon atoms that may have a substituent.

2. The organic electroluminescent device of claim 1, wherein the capping layer has a thickness in a range of 30 nm to 120 nm.

3. The organic electroluminescent device of claim 1, wherein the capping layer has a refractive index of 1.50 or more for light passing through the capping layer within the wavelength range of 400 nm to 750 nm, and has small refractive index differences in blue, green, and red wavelength regions.

4. A method for using a compound represented by the following general formula (F) for a capping layer of an organic electroluminescent device (1′)

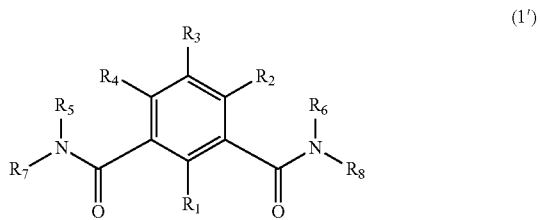

wherein $R_1$ represents a hydrogen atom or a deuterium atom;
$R_2$ represents a hydrogen atom or a deuterium atom;
$R_3$ represents a hydrogen atom, a deuterium atom, a linear or branched alkyl of 1 to 8 carbon atoms or a substituted or unsubstituted aromatic hydrocarbon group;
$R_4$ represents a hydrogen atom, a deuterium atom, a fluorine atom, a chlorine atom, a bromine atom, or an iodine atom;
$R_5$ and $R_6$ may be the same or different, and represent a hydrogen atom or a deuterium atom; and
$R_7$ and $R_8$ may be the same or different, and represent cycloalkyl of 5 to 10 carbon atoms that may have a substituent.

* * * * *

UNITED STATES PATENT AND TRADEMARK OFFICE
CERTIFICATE OF CORRECTION

PATENT NO. : 9,882,136 B2
APPLICATION NO. : 14/402219
DATED : January 30, 2018
INVENTOR(S) : Makoto Nagaoka et al.

It is certified that error appears in the above-identified patent and that said Letters Patent is hereby corrected as shown below:

In the Claims

At Column 29, Claim number 1, Line number 1, Add next to the formula: (1′)

At Column 30, Claim number 4, Line number 2, Delete: "(F)", and replace with: (1′)

Signed and Sealed this
Twenty-ninth Day of January, 2019

Andrei Iancu
*Director of the United States Patent and Trademark Office*